United States Patent [19]

Cutler et al.

[11] Patent Number: 4,572,208
[45] Date of Patent: Feb. 25, 1986

[54] METABOLIC GAS MONITORING APPARATUS AND METHOD

[75] Inventors: Christopher A. Cutler, Bountiful; William D. Wallace; Dwayne R. Westenskow, both of Salt Lake City, all of Utah

[73] Assignee: Utah Medical Products, Inc., Midvale, Utah

[21] Appl. No.: 745,820

[22] Filed: Jun. 17, 1985

Related U.S. Application Data

[63] Continuation of Ser. No. 509,209, Jun. 29, 1983, abandoned.

[51] Int. Cl.$^4$ ................................................ A61B 5/08
[52] U.S. Cl. ..................................... 128/718; 128/719
[58] Field of Search ............... 128/718, 719; 436/68; 204/424, 427

[56] References Cited

U.S. PATENT DOCUMENTS

| | | | |
|---|---|---|---|
| 2,792,828 | 5/1957 | Engelder | 128/718 |
| 3,507,146 | 4/1970 | Webb | 128/718 |
| 3,514,377 | 5/1970 | Spacil et al. | 128/719 |
| 3,895,630 | 7/1975 | Bachman | 128/2.07 |
| 4,075,481 | 2/1978 | Stoft et al. | 250/343 |
| 4,080,103 | 3/1978 | Bird | 417/3 |
| 4,211,239 | 7/1980 | Raemer et al. | 128/718 |
| 4,231,256 | 11/1980 | Chapman et al. | 73/421.5 |
| 4,233,842 | 11/1980 | Raemer et al. | 73/861.04 |
| 4,368,740 | 1/1983 | Binder | 128/718 |
| 4,430,192 | 2/1984 | Maeda | 204/427 |
| 4,440,177 | 4/1984 | Anderson et al. | 128/719 |

OTHER PUBLICATIONS

L. G. Wong et al., "Eliminating the Effect of Water Vapor in Respiratory Gas Analysis," 7 Journal of Clinical Engineering (No. 2), pp. 159-163 (Apr.-Jun. 1982).
A. C. Norton, "Development and Testing of a Microprocessor-Controlled System for Measurement of Gas Exchange and Related Variables in Man During Rest and Exercise," Beckman Reprint No. 025 (1982).
N. S. Deno et al., "A Dryer for Rapid Response On-Line Expired Gas Measurements," 46 J. Appl. Physiol.: Respirat. Environ. Exercist Physiol. (No. 6) pp. 1196-1199 (1979).
J. H. Willmore et al., "An Automated System for Assessing Metabolic and Respiratory Function During Exercise," 40 Journal of Applied Physiology (No. 4) pp. 619-624 (Apr. 1976).
J. H. Willmore et al., "Semiautomated Systems Approach to the Assessment of Oxygen Uptake During Exercise," 36 Journal of Applied Physiology (No. 5), pp. 618-620 (May 1974).
W. J. Beaver, "Water Vapor Corrections in Oxygen Consumption Calculations" 35 Journal of Applied Physiology (No. 6) pp. 928-931 (Dec. 1973).

(List continued on next page.)

*Primary Examiner*—Edward M. Coven
*Assistant Examiner*—Max F. Hindenburg
*Attorney, Agent, or Firm*—Workman, Nydegger & Jensen

[57] ABSTRACT

Metabolic gas monitoring apparatus and methods for measuring the metabolic rate in patients. The apparatus includes separate inlets for a calibration gas, inspired gas, and expired gas, and means for alternately introducing each gaseous sample into a thermoelectric cooler. The cooler is configured with relatively narrow passageways so as to contain a minimal amount of gaseous volume therein and thus provides for a more dynamic response time and for more accurate measurements. The apparatus further includes a carbon dioxide sensor and an oxygen sensor for measuring the concentration of carbon dioxide and oxygen, respectively, in the gaseous samples, and a microprocessor for comparing the measured concentrations of carbon dioxide and oxygen in the inspired gas and expired gas and for calculating the metabolic rate. Preferably, the oxygen sensor has a zirconium oxide differential electrode and a substantially equal pressure is maintained in a sample chamber and a reference chamber of the oxygen sensor.

22 Claims, 3 Drawing Figures

OTHER PUBLICATIONS

G. Lister et al., "Oxygen Uptake in Infants and Children: A Simple Method for Measurement," *Pediatrics*, vol. 53, No. 5, pp. 656–662 (May 1974).

P. Swyer et al., "Energy Metabolism and Substrate Utilisation During Total Parenteral Nutrition in the Newborn," *Intensive Care of the Newborn, II*, pp. 307–316 (U.S.A., 1978).

K. Wasserman et al., "Anaerobic Threshold and Respiratory Gas Exchange During Exercise," 35 Journal of Applied Physiology (No. 2), pp. 236–243 (Aug. 1973).

J. H. Auchincloss, Jr. et al., "Control of Water Vapor During Rapid Analysis of Respiratory Gases in Expired Air," 28 Journal of Applied Physiology (No. 2), pp. 245–247.

Advertisement of the Puritan-Bennett Corp., Kansas City, Missouri 64106, entitled "The $CO_2$ Monitoring System Features . . . ".

M. D. Cunningham, "Monitoring Pulmonary Function During Mechanical Ventilation of Infants with RDS," *Respiratory Therapy*, pp. 45 and 47–53d (May/Jun. 1983).

P. Swyer, Notes on Responses to Questions (Sep. 1983).

Hans Rudolph, Inc., "Rudolph Pneumotachometer" (Aug. 17, 1983).

Hans Rudolph, Inc., "New Product: Miniature 2-Way Non-Rebreathing Valve, Model No. 2384 Rabbit Valve" (Oct. 1982).

Hans Rudolph, Inc., "New Product: Model No. 2300 Rat Valve Miniature, 2-Way Non-Rebreathing Valve" (Apr. 1981).

Kipp and Zonen, "Metabolic Rate Measurement: Universal Diaferometer MG 4" (Holland, Jul. 1968).

G. Olsen et al., "Ventilatory Response to Carbon Dioxide of Infants Following Chronic Prenatal Methadone Exposure," *Journal of Pediatrics*, vol. 96, No. 6, pp. 983–989 (1980).

D. Raemer et al., "A Method for Measurement of Oxygen Uptake in Neonates," *Journal of the American Physiological Society*, pp. 1200–1204 (1979).

METABOLIC GAS MONITORING APPARATUS AND METHOD

This application is a continuation of U.S. application Ser. No. 509,209, filed June 29, 1983, for Metabolic Gas Monitoring Apparatus and Method, now abandoned.

BACKGROUND

1. Field of the Invention

The present invention relates to metabolic gas monitoring apparatus and methods, and in particular, to apparatus and methods for measuring the metabolic rate of patients.

2. The Prior Art

Prior art systems for monitoring the metabolic rate of human patients are well-known. In such systems, the amount of oxygen ($O_2$) and carbon dioxide ($CO_2$) are measured in both the gas inspired by the patient and the gas expired by the patient, and the amounts of oxygen consumed and carbon dioxide produced are calculated so as to determine the metabolic rate of the patient. Oxygen and carbon dioxide sensors are typically used for this purpose. The amount of oxygen consumed and the amount of carbon dioxide produced by a living subject reflects the nutritional and metabolic status of the body. Accurate measurement of these parameters may thus be extremely helpful in the treatment of various patients.

The measurement of the oxygen consumption rate and the carbon dioxide production rate in an individual serves, for example, as an indicator of relative changes in cardiovascular function and tissue perfusion, which must be carefully monitored in critically ill patients. Typically, there is an increase of catabolism of protein and an associated loss of body weight resulting from the breakdown of tissue required to supply energy for the dramatic metabolic requirements in critically ill patients, thus providing further reason for careful monitoring of the metabolic rate. In burn patients, the metabolic rate may increase by fifty to three hundred percent (50%-300%).

Additionally, measurement of a patient's metabolic rate is useful in calculating the energy expenditure for a patient with regard to surgery, infection, or injury. Careful measurement of the metabolic rate can provide an accurate basis for formulating a dietary plan for the patient, and thus ensure that the patient's caloric intake is properly coordinated to avoid lipogenesis and other adverse physiological consequences of excess caloric consumption. Also, measurement of the metabolic rate is useful in determining a patient's response to exercise, and is often used in stress test measurement.

One disadvantage of many prior art systems for measuring the metabolic rate is that typically the apparatus employed are complex and expensive, since the apparatus are not combined into a single compact unit. These systems are generally cumbersome to move and require expert attendance for accurate operation.

Another problem encountered in prior art systems for measuring the metabolic rate of a patient is the presence of water vapor in the inspired and expired gas. Gaseous samples of inspired air typically have a water vapor partial pressure of about 0-25 torr. Moreover, in patients receiving ventilatory support in which the inspired gas is humidified, the water vapor pressure typically varies between 0 and about 47 torr. Gaseous samples of a patient's expired gas typically have a water vapor partial pressure of about 47 torr. Since water vapor may be detected by the oxygen sensor and may adversely affect the accuracy of the oxygen sensor, the prior art has sought to remove water vapor from the inspired and expired gas.

Moreover, another detrimental effect of water vapor on respiratory gas analysis is that the partial pressure of the water displaces the analyzed inspired or expired gas, thereby further resulting in inaccurate readings. Another associated problem is the error introduced if the water vapor concentration in the inspired gas is not equivalent to the water vapor concentration in the expired gas. Such equalization is needed to cancel out the effects of water vapor when the oxygen concentrations of the inspired and expired gases are compared.

One attempt to remove water vapor from the expired gases prior to analysis resulted in physically drying the expired gas, for example, by introducing the expired gas into a desiccator. One system has been developed using a desiccator filled with calcium sulfate ($CaSO_4$) as the drying agent. Such desiccator systems experience at least two significant problems: (1) the drying agent must be carefully watched and replaced on a regular basis, and (2) the volume within the desiccator required to perform the drying makes for increased dead space within the system and thus results in a longer "washout time" for measuring changes in gaseous composition. As used herein, the term "washout time" refers to the amount of time which is needed for a unit of gaseous sample to wash out or displace the gas already within the system.

Washout time is an important factor in monitoring changes in the oxygen and carbon dioxide concentrations within the inspired and expired gases. Where large total volumes or dead volumes are present within a metabolic gas monitoring system, corresponding large washout times are created, resulting in decreased ability to quickly and accurately measure changes in the composition of the inspired and expired gases. Indeed, in prior art systems employing a desiccator to dry expired gases, a breath-by-breath analysis of the patient's expired gases is extremely difficult, if not impossible. Again, this is because the long washout times in such systems do not allow for the dynamic response to changes in the oxygen and carbon dioxide concentrations in breath-by-breath analyses of expired gas. Thus, large total volumes and dead volumes within such prior art systems has resulted in less sensitivity to changes in the composition of the gases analyzed and less accurate measurements of the oxygen and carbon dioxide components of the gases.

PRINCIPAL OBJECTS AND BRIEF SUMMARY OF THE INVENTION

It is, therefore, an object of the present invention to provide a metabolic gas monitoring apparatus configured as a single, compact unit which is less expensive to manufacture than the multicomponent prior art apparatus.

Another object of the present invention is to provide a metabolic gas monitoring apparatus and method wherein a substantial portion of the water vapor is removed from the expired gas sample to be analyzed and wherein the water vapor concentration in the calibration gas and inspired gas is substantially equalized with the remaining low water vapor concentration in the expired gas.

Still another object of the present invention is to provide a metabolic gas monitoring apparatus and method wherein vapor is effectively removed without creating large total volumes or dead volumes, thereby substantially eliminating the problems associated with long washout times.

A further object of the present invention is to provide a metabolic gas monitoring apparatus and method which is more sensitive to changes in the composition of the gaseous samples analyzed, which compensates for pressure fluctuations in the apparatus, and which provides more accurate measurements of the oxygen and carbon dioxide within the gaseous samples.

Yet another object of the present invention is to provide an improved apparatus and method for measuring the metabolic rate of a patient by monitoring the patient's consumption of oxygen and production of carbon dioxide.

These and other objects and features of the present invention will become more fully apparent from the following description and appended claims, taken in conjunction with the accompanying drawings.

The present invention comprises a novel metabolic gas monitoring apparatus and method for measuring the metabolic rate of patients. In one presently preferred embodiment, the apparatus includes separate inlet tubing for introducing a calibration gas, inspired gas, and expired gas (either averaged over a short period of time or in a breath-by-breath mode, e.g. end-tidal mode) into the apparatus. A thermoelectric cooler is disposed within the apparatus and a switching mechanism is provided so as to alternately regulate the flow of the calibration gas, the inspired gas, or the expired gas from the inlet tubing to the cooler. The cooler is preferably configured as a rectangular block having three passageways formed therein.

A horizontal passageway is formed in the cooler for carrying a gaseous sample through the cooler and allowing the gaseous sample to reach equilibrium temperature with the cooler. In the case of expired gas, as the gaseous sample travels through the horizontal passageway, water vapor condenses from the expired gas and is removed through a lower vertical passageway. The remaining sample of expired gas exits the cooler through an upper vertical passageway. If the gaseous sample is relatively dry (e.g., a calibration gas), the sample picks up water vapor within the cooler as it reaches the equilibrium temperature of the cooler. Thus, the cooler acts both to remove a substantial amount of water vapor from the expired gas and also to equalize the water vapor concentration in the calibration gas, the inspired gas, and the expired gas according to the equilibrium temperature of the cooler.

The passageways formed in the cooler preferably have substantially the same diameter as the inlet tubing for introducing the calibration, inspired, and expired end-tidal gaseous samples into the apparatus. Thus, large total volumes and dead volumes are not experienced within the cooler, and the washout time needed to purge the cooler of a certain gaseous sample is minimized. After passing through the cooler, the gaseous sample is sent to a carbon dioxide sensor and to an oxygen sensor wherein the concentrations of carbon dioxide and oxygen, respectively, are detected and measured. Minimization of the total volume and dead volume, and thus of washout time within the apparatus results in greater sensitivity to changes in the composition of the gaseous samples analyzed and more accurate measurements of the oxygen and carbon dioxide within the gaseous samples.

In one presently preferred embodiment, the oxygen sensor has a zirconium oxide differential electrode and the pressure within a reference chamber and a sample chamber of the oxygen sensor are kept substantially equal at all times. The apparatus further includes a microprocessor for collecting the data as sensed by the carbon dioxide and oxygen sensors and for calculating the metabolic rate of the patient from this data.

DETAILED DESCRIPTION OF THE PREFERRED EMBODIMENTS

Figure 1:
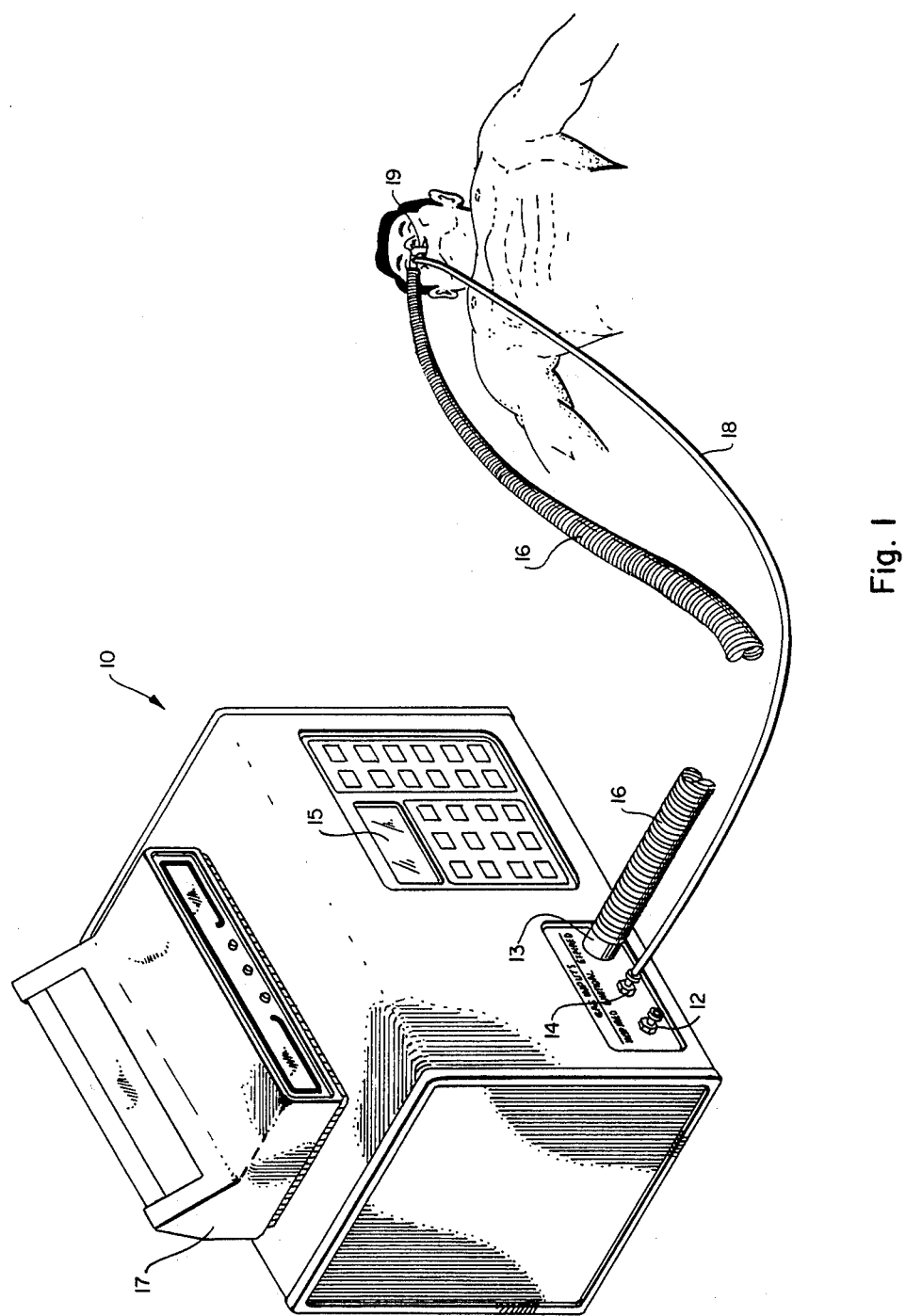
FIG. 1 is a general perspective illustration of metabolic gas monitoring apparatus of the present invention illustrating use of the apparatus with a patient.

Reference is now made to the drawings wherein like parts are designated with like numerals throughout. Referring to FIG. 1, the metabolic gas monitoring apparatus of the present invention, generally designated 10, is shown in operation. Metabolic gas monitoring apparatus 10 includes a first inlet 12 for sampling gas inspired by the patient, and a second inlet 13 for sampling the gas expired by the patient through a tube 16.

The inspired gas directly enters first inlet 12 when the inspired gas is ambient gas from the room. Where the patient is inspiring gas from a ventilation or anesthesia circuit, a tube (not shown) is provided to connect the ventilation or anesthesia circuit to first inlet 12. One end of tube 16 is connected to the second inlet 13 of the apparatus and the other end is connected by way of a nonrebreathing valve (not shown) within a mouthpiece 19 or endotracheal tube (not shown) which is inserted into the patient's mouth.

An end-tidal inlet 14 is also provided for conducting a breath-by-breath analysis of the expired gas from the patient. A tube 18 is connected to mouthpiece 19 at one end thereof and to end-tidal inlet 14 at the other end thereof to provide for a breath-by-breath analysis of the expired gas. Tube 16 is larger in diameter than tube 18 and is of sufficient size to accommodate the gas expired by the patient without experiencing significant resistance to the flow of the expired gas. Metabolic gas monitoring apparatus 10 also includes a control panel 15 having a digital display readout, and a printer 17 with graphics capability for trend recording of output data.

Figure 2:
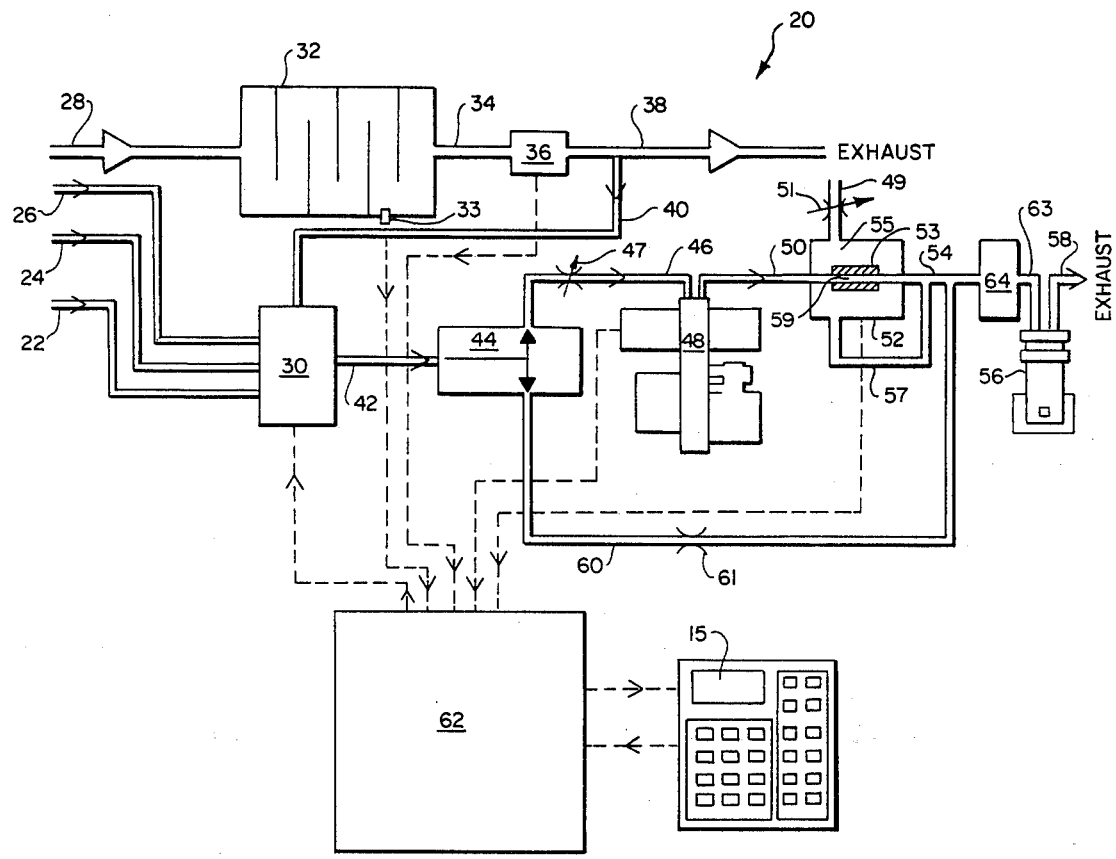
FIG. 2 is a schematic diagram of a presently preferred embodiment of the metabolic gas monitoring apparatus and method of the present invention.

Referring now to FIG. 2, a schematic illustration of a presently preferred embodiment of the metabolic gas monitoring apparatus and method of the present invention, generally designated 20, is illustrated. The schematic diagram of apparatus 20 in FIG. 2 effectively illustrates the various components within the apparatus 10 shown in FIG. 1; thus apparatus 10 and apparatus 20 actually comprise a single preferred embodiment of the present invention.

Metabolic gas monitoring apparatus 20 is provided with a calibration gas inlet conduit 22, which is in gaseous communication with a cylinder of calibration gas (not shown) which would typically be mounted externally to apparatus 10 shown in FIG. 1. Apparatus 20 is also provided with an inspired gas inlet conduit 24 which is in gaseous communication with inlet 12, an end-tidal expired gas inlet conduit 26 which is in gaseous communication with inlet 14, and an expired gas inlet conduit 28 which is in gaseous communication with inlet 13.

Gas inlet conduits 22, 24, 26, and 28 thus provide for the introduction of calibration gas, inspired gas, expired gas (in a breath-by-breath mode), and expired gas (averaged over a short period of time), respectively, into apparatus 20. As shown in FIG. 2, gas inlet conduit 28 has a larger diameter than gas inlet conduits 22, 24, and 26 so as to ensure unrestricted flow of expired gas through conduit 28.

Expired gas inlet conduit 28 is in communication with a mixing chamber 32 having a temperature sensor 33. A conduit 34 provides for communication between the mixing chamber 32 and a flow meter 36, while conduit 40 provides for conducting the expired gas sample away from flow meter 36 and further into the apparatus as will be explained in more detail hereinafter. Another conduit 38 is used to exhaust excess sampled gas. Flow meter 36 may be any suitable conventional flow meter; for example, the "VF-563D" flow meter manufactured by J-Tec, Cedar Rapids, Iowa, has been found to be suitable for purposes of the present invention.

Gas inlet conduits 22, 24, 26 and 40 are in direct communication with a series of electronically actuated solenoid valves which form a switching mechanism 30. Separate solenoid valves of switching mechanism 30 operate to control the flow of gas through each of gas inlet conduits 22, 24, 26, and 40. Thus switching mechanism 30 provides for the alternate introduction of a gaseous sample from one of gas inlet conduits 22, 24, 26, and 40 into another gas conduit 42. Switching mechanism 30 may be any suitable conventional solenoid valve system; for example, the "LIF Series" of solenoid valves manufactured by the Lee Company, Westbrook, Conn., has been found to be suitable for purposes of the present invention.

Figure 3:
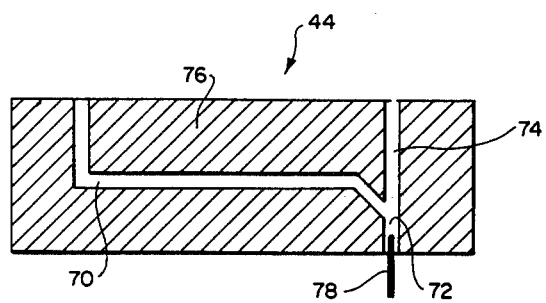
FIG. 3 is a cross-sectional view of a presently preferred embodiment of a cooler used to remove water vapor in accordance with the apparatus and method of the present invention.

Gas conduit 42 provides for the introduction of the gaseous sample from one of gas inlet conduits 22, 24, 26, and 40 into a thermoelectric cooler 44. Preferably, cooler 44 is constructed of an aluminum block with a thermoelectric element (not shown) which employs the well-known Peltier effect to cool the cooler 44. The internal configuration of a presently preferred embodiment of cooler 44 is illustrated in FIG. 3. As seen in FIG. 3, cooler 44 includes a block 76 in which is formed three passageways: a substantially horizontal passageway 70; a lower vertical passageway 72; and an upper vertical passageway 74. A wick 78 may be disposed within passageway 72 for purposes to be hereinafter more fully explained. Preferably, cooler 44 produces cooling by the Peltier-effect so as to cool gas samples flowing through passageway 70 to a temperature of about 0°–15° C., and preferably in the range of about 8°–12° C. The operation of cooler 44 will be explained in more detail hereinafter.

Referring again to FIG. 2, a conduit 46 provides for gaseous communication between passageway 74 of cooler 44 and a carbon dioxide sensor 48. Sensor 48 may be any suitable conventional carbon dioxide sensor; for example, the "Series V" carbon dioxide sensor manufactured by Sensors, Inc., Saline, Mich., has been found to be suitable for purposes of the present invention. A needle valve 47 is mounted within conduit 46 so as to allow for the adjustment and control of the flow of gas passing through conduit 46.

Another conduit 50 provides for gaseous communication between carbon dioxide sensor 48 and an oxygen sensor 52 which is shown in cross-section in FIG. 2. A conduit 54 provides for communication between oxygen sensor 52 and a filter 64, while a conduit 63 provides for communication between filter 61 and a pump 56. Pump 56 serves to draw the gaseous samples from conduit 54, through filter 61 and conduit 63, and into an exhaust conduit 58 after analysis, while filter 64 acts to filter out impurities to protect pump 56.

A conduit 60 is also provided between passageway 72 of cooler 44 and gas conduit 54 to allow for the removal of gas and condensed water from the cooler to the exhaust. A fixed restrictor 61 is provided within conduit 60 to restrict flow through conduit 60. One fixed restrictor which has been found to work well for purposes of the present invention is the "Visco Jet" viscosity independent restrictor manufactured by the Lee Company, Westbrook, Conn. One advantage of this viscosity independent restrictor is that it creates high resistance to the flow of gas while permitting a relatively large diameter for conduit 60 so that water may pass freely through the resistor.

In one presently preferred embodiment, oxygen sensor 52 is comprised of a zirconium oxide ($ZrO_2$) tube 53 which acts as a differential electrode. A reference gas (typically room air) having a relatively constant oxygen concentration is introduced through a conduit 49 and into a reference chamber 55 of oxygen sensor 52. A variable restrictor or needle valve 51 controls the flow of the reference gas into the reference chamber. A conduit 57 provides for gaseous communication between reference chamber 55 and conduit 54. A sample chamber 59 within zirconium oxide tube 53 provides for passage of a gaseous sample through oxygen sensor 52, sample chamber 59 being in gaseous communication with conduits 50 and 54.

The operation of oxygen sensor 52 will be best understood from the following discussion. The gaseous sample to be analyzed (whether the calibration gas, the inspired gas, or the expired gas) enters sample chamber 59 of sensor 52 from conduit 50 and exits the sample chamber 59 into conduit 54. The reference gas enters conduit 49 into reference chamber 55, and exits the reference chamber through conduit 57. The reference gas then joins the gaseous sample at conduit 54, and the combined gas is withdrawn by pump 56 through filter 64 and conduits 63 and 58. The electric potential differential imposed on zirconium oxide differential electrode 53 during passage of the reference and sample gases through sensor 52 is measured, and this data is electronically signalled to the microprocessing unit 62 for calculation of the concentration of oxygen in the gaseous sample passing through sample chamber 59.

Since sample chamber 59 and reference chamber 55 are in gaseous communication with each other by virtue of conduits 54 and 57, the absolute pressures within chambers 55 and 59 are substantially equal at all times. Although other oxygen sensors mqy be used with the present invention, an oxygen sensor having the pressure equalization features of the oxygen sensor 52 in the embodiment of FIG. 2 is presently preferred. The importance of such an oxygen sensor will be explained in more detail hereinafter. One oxygen sensor having such pressure equalization features and which has been found to be suitable for purposes of the present invention is the "Series 6" zirconium oxide oxygen sensor manufactured by Sensors, Inc., Saline, Mich.

Apparatus 20 also includes a microprocessor 62 which receives signals from various components of apparatus 20 and uses them to calculate the metabolic rate. For example, microprocessor 62 receives data as to the carbon dioxide and oxygen concentrations sensed in carbon dioxide sensor 48 and oxygen sensor 52, respectively. Moreover, microprocessor 62 receives temperature data from the temperature sensor 33 within mixing chamber 32, flow rate data from flow meter 36, and controls the positioning of switching mechanism 30. After comparing the relative concentrations of carbon dioxide and oxygen in the inspired gas and expired gas, microprocessor 62 calculates the metabolic rate of the patient and displays this information on a display unit 15. Microprocessor 62 is any suitable conventional microprocessing system; for example, microprocessing systems manufactured by Rockwell International, Anaheim, Calif., have been found to be suitable for purposes of the present invention. In particular, a microprocessor employing the "Rockwell 6502" circuit as the controlling integrated circuit has been found to be suitable.

The operation of apparatus 20 and a presently preferred embodiment of the method of the present invention will be best understood from the following discussion. Initially, carbon dioxide sensor 48 and oxygen sensor 52 must be calibrated. To accomplish this, the microprocessor 62 signals switching mechanism 30 to allow entry of the calibration gas through conduit 22 and into conduit 42. The calibration gas flows through cooler 44, gas conduit 46, and into carbon dioxide sensor 48. The calibration gas then passes from carbon dioxide sensor 48 through gas conduit 50 and into oxygen sensor 52. The gas is then pumped by pump 56 through gas conduit 54 and 58 to the exhaust. The measured concentrations of oxygen and carbon dioxide are then signaled to microprocessor 62 for calibration of the system.

In the calibration of carbon dioxide sensor 48, generally two calibration gases are needed. Typically, a commercially available calibration gas containing 10% carbon dioxide, 21% oxygen, and 69% nitrogen is used to calibrate carbon dioxide sensor 48,, and this calibration gas is introduced into the apparatus through conduit 22. It will be appreciated, however, that any other calibration gas may be used. For example, a calibration gas containing 10% carbon dioxide, 15% oxygen, and 75% nitrogen is also typically used. For the second calibration gas, typically, ambient air is introduced through gas inlet conduit 24 and into apparatus 20 in the same manner as with the first calibration gas. The ambient air provides a second calibration point (approximately a zero reference point) for calibrating carbon dioxide sensor 48.

In the calibration of oxygen sensor 52, only one calibration gas, such as the calibration gas described above comprising 10% carbon dioxide, 21% oxygen, and 69% nitrogen, is needed where a zirconium oxide sensor such as that described herein is employed. Since the electric potential of the zirconium oxide oxygen sensor decreases logarithmically with a decrease in oxygen concentration instead of linearly as is true with other oxygen sensors and since the logarithmic response is stable over long periods of time, only one reference point and thus only one calibration gas is needed to calibrate the oxygen sensor 52.

After sensors 48 and 52 of apparatus 20 have been calibrated, microprocessor 62 signals switching mechanism 30 to allow a sample of inspired gas to flow through gas conduit 24 and into gas conduit 42. The inspired gas then passes through cooler 44, gas conduit 46, and into carbon dioxide sensor 48 which measures the amount of carbon dioxide in the sample. The inspired gas then passes through gas conduit 50 and into oxygen sensor 52 which measures the amount of oxygen in the inspired gas sample. Pump 56 removes the gaseous sample through conduits 54 and 58. Subsequently, microprocessor 62 instructs switching mechanism 30 to allow expired gas to enter the apparatus 20 through gas conduit 40.

In this mode, the average metabolic rate over a short period of time will be measured. Expired gas from the patient first enters gas conduit 28 and flows into mixing chamber 32 so as to average several breaths expired by the patient. The temperature of the expired gas within mixing chamber 32 is measured by temperature sensor 33 and this temperature data is communicated to microprocessor 62. The mixed expired gas exits mixing chamber 32 through gas conduit 34 and passes through flow meter 36 where the expiration flow rate of the patient is measured.

After measuring the flow rate of the expired gas through flow meter 36, the value for the flow rate is reported to the microprocessor 62 and the expired gaseous sample enters gas conduit 40 and flows through switching mechanism 30 into gas conduit 42. From this point, the expired gas follows the same path through apparatus 20 as for the calibration gas and inspired gas, passing through cooler 44 and sensors 48 and 52 and exiting through the exhaust. Again, the carbon dioxide and oxygen concentrations in the expired gas sample are measured by sensors 48 and 52 and are compared with those for the inspired gas sample by microprocessor 62. Microprocessor 62 then calculates the metabolic rate and the results are displayed at display unit 15 and/or printed at printer 17.

In the breath-by-breath mode, only the concentration of carbon dioxide and oxygen in each breath are measured, and the metabolic rate is not calculated. Thus, in such an analysis, apparatus 20 is first calibrated as discussed hereinabove and then switching mechanism 30 allows entry of expired end-tidal gas through gas conduit 26 and through apparatus 20 in the same fashion as for the calibration gas. The carbon dioxide and oxygen concentrations in each breath are measured by sensors 48 and 52, respectively, and the data is reported to microprocessor 62 and displayed at display unit 15 and/or printed at printer 17.

The present invention achieves accurate measurements of the carbon dioxide and oxygen concentrations within the gaseous samples and responds to rapid changes or fluctuations in gaseous composition. One of the important features of the present invention which provides these advantages is the configuration and operation of thermoelectric cooler 44. The operation of cooler 44 is discussed below.

As expired gas enters passageway 70 of cooler 44, the gas immediately begins to be cooled to the temperature of the cooler so as to be in equilibrium therewith. The relatively long horizontal portion of passageway 70 allows the expired gas sample adequate time to reach temperature equilibrium with cooler 44. Water vapor condenses out of the expired gas sample as the sample cools to the equilibrium temperature of cooler 44, and the condensed water flows downwardly through the angled end of passageway 70 and into vertical passageway 72. The removal of water from passageway 72 of cooler 44 is assisted by wick 78.

After removal of the water from the expired gas sample, the major portion of the expired gas sample exits cooler 44 through passageway 74, with a minor portion of the expired gas sample exiting through passageway 72 so as to assist in the removal of the condensed water from the cooler. For example, it has been found desirable to adjust needle valve 47 and to configure fixed restrictor 61 such that about 80% of the expired gas sample exits cooler 44 through passageway 74, with the remaining 20% of the expired gas sample exiting cooler 44 with the condensed water through passageway 72.

The calibration gas is typically drier than the saturation point for the calibration gas at the equilibrium temperature of the cooler 44. Thus, when the calibration gas is passed through cooler 44, it will pick up a very small portion of water vapor from cooler 44 as it is cooled to the equilibrium temperature of the cooler. Similarly, depending upon its initial water vapor content, the inspired gas sample will either pick up or condense out water vapor as it passes through cooler 44, so that the water vapor concentration of the inspired gas corresponds to the saturation point of the equilibrium temperature of cooler 44. Thus, cooler 44 serves not only to remove a substantial portion of water from the expired gas sample so as to minimize the detection of water by oxygen sensor 52, but cooler 44 also serves to equalize the water vapor concentration in all gaseous samples passing through the cooler so as to cancel out the effects of the water vapor.

Preferably, passageways 70, 72, and 74 of cooler 44 are formed so as to be relatively narrow, for example, of approximately the same cross-sectional area as gas inlet conduits 22, 24, and 26. Passageways 70, 72, and 74 may be constructed of any desired cross-sectional shape, as long as they are constructed relatively narrow. The small volume occupied by passageways 70, 72, and 74 within cooler 44 thus provides for a minimal amount of total gaseous volume and dead volume within cooler 44 and thus serves to minimize the washout time within the cooler and the apparatus. Consequently, more accurate measurements are achieved by sensors 48 and 52, and less time is needed in order for sensors 48 and 52 to respond to a change in the oxygen and carbon dioxide concentrations within a gaseous sample, and in particular, the expired gas. Importantly, the dynamic response of apparatus 20 to changes in gaseous composition permits even a breath by breath analysis of the expired gas from the patient. Thus, the configuration of cooler block 44 is important in achieving the improved results of the present invention.

In one application of the present invention, gas inlet conduits 22, 24, and 26 were constructed with an inner diameter of about 0.062 inches. In this application, cooler block 76 was constructed of a piece of aluminum 4 inches long, 1 inch wide, and 1.5 inches high. The cross-sectional area of cooler passageways 70, 72, and 74, was substantially the same as that for gas inlet conduits 22, 24, and 26. The length of the horizontal portion of passageway 70 was about 3 inches. These dimensions for the gas inlet conduits 22, 24, and 26 and cooler 44 are suitable for a gas sample flow of about 50-100 millimeters per minute. It will be recognized that other dimensions may be more preferable for other sample flows.

Another important feature of the present invention is the oxygen sensor comprising a zirconium oxide differential electrode and a having substantially equal pressure in the reference chamber and sample chamber of the sensor at all times. The pressure equalization between the reference and sample chambers provides for more accurate measurements of the oxygen concentration within sensor 52. Further, as mentioned previously, the zirconium oxide-type oxygen sensor 52 requires only a single calibration gas for calibrating the oxygen sensor.

The fact that the pressure within the reference chamber of the oxygen sensor of the present invention is substantially the same as the pressure within the sample chamber of the oxygen sensor at all times, becomes important as the flow rate of gas passing through the sample chamber of the oxygen sensor 52 changes, for example, as the breathing rate of the patient changes. Prior art oxygen sensors have typically been adversely sensitive to changes in pressure. Thus, pressure changes within conventional metabolic gas monitoring systems have typically had an adverse effect on the accuracy of prior art oxygen sensors. Such error is especially pronounced when the patient is on a ventilator circuit, since the inspired gas flowing through a ventilator circuit typically experiences significant pressure fluctuations.

The present invention provides a method for compensating for pressure fluctuations so as to substantially avoid the error introduced by such pressure fluctuations in the prior art. For example, suppose the flow rate within apparatus 20 of the present invention increases due to an increase in the expiration rate of the patient. This, of course, causes the pressure in the sample chamber 59 of sensor 52 to increase. Due to the gaseous communication between chambers 55 and 59, the pressure within the reference chamber 55 of sensor 52 also increases until the pressure is again substantially equal in chambers 55 and 59. The absolute pressures within the sample chamber and the reference chamber of oxygen sensor 52 therefore remain substantially equal at all times, resulting in more accurate measurements of the partial pressure of oxygen measured by sensor 52. Thus, the present invention provides an apparatus and method for substantially eliminating the problems caused by pressure fluctuations within the prior art oxygen sensors and apparatus.

Additionally, the zirconium oxide sensor used with the present invention has a better dynamic response time (100-200 milliseconds for 90% measurement) to changes in oxygen concentration within a gaseous sample. This is in contrast to response times of about one second or greater for prior art oxygen sensors, such as polarographic sensors, to measure 90% of the change.

The apparatus of the present invention can be operated as an independent system, or in tandem with an anesthesia or ventilation circuit of a patient who is on anesthesia or who is receiving oxygen ventilation. It will be appreciated that other applications of the present invention to other systems may also be possible.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by U.S. Letters Patent is:

1. An apparatus for measuring the metabolic rate of a patient, comprising:
   (a) a first inlet conduit for receiving expired gas from the respiratory system of a patient;
   (b) a second inlet conduit for receiving gas as inspired by the patient;
   (c) a third inlet conduit for receiving a calibration gas;
   (d) an outlet conduit;
   (e) regulating means, positioned between said inlet conduits and said outlet conduit, for alternately regulating a continuous flow through said outlet conduit of one of said expired gas from the first inlet conduit, inspired gas from the second inlet conduit, or calibration gas from the third inlet conduit, said regulating means thereby serving to alternately allow passage of one gas at a time through said outlet conduit;
   (f) a cooler for cooling gas passing therethrough, said cooler being in gaseous communication with said outlet conduit so as to be positioned on the output side of said regulating means and said cooler serving to remove water from or add water vapor to the gas continuously flowing from said regulating means as needed to approximately equalize the water vapor pressure of each gas flowing through said cooler;
   (g) first sensing means in communication with the cooler for measuring the amount of carbon dioxide in a gaseous sample;
   (h) second sensing means in communication with the cooler for measuring the amount of oxygen in a gaseous sample; and
   (i) means for comparing the amounts of carbon dioxide and oxygen in one gaseous sample with those in another gaseous sample.

2. An apparatus as defined in claim 1 wherein the cooler is configured with passageways of substantially similar cross-sectional area as the second and third inlet conduits.

3. An apparatus as defined in claim 1 further comprising a mixer chamber disposed between and in gaseous communication with the first inlet conduit and said regulating means, said mixing chamber serving to mix the expired gas from the first inlet conduit.

4. An apparatus as defined in claim 3 further comprising means for measuring the flow of expired gas between the mixing chamber and said regulating means.

5. An apparatus as defined in claim 1 further comprising a fourth inlet conduit for receiving expired gas from the patient in a breath-by-breath mode, said regulating means being capable of alternately regulating the flow of expired gas from the first inlet conduit, inspired gas from the second inlet conduit, calibration gas from the third inlet conduit, or expired gas from the fourth inlet conduit.

6. An apparatus as defined in claim 1 wherein the cooler has a first horizontal passageway for carrying a gaseous sample through the cooler, a second lower vertical passageway for continuously removing water which condenses within the cooler, and a third upper vertical passageway for removing the gaseous sample from the cooler.

7. An apparatus as defined in claim 6 wherein the majority of the gaseous sample is removed through the third passageway of the cooler and wherein the remaining portion of the gaseous sample is removed through the second passageway of the cooler so as to assist in the removal of condensed water from the cooler.

8. An apparatus as defined in claim 6 further comprising a wick disposed within the second vertical passageway for absorbing and continuously transporting condensed water from the cooler.

9. An apparatus as defined in claim 1 wherein the cooler is a thermoelectric cooler.

10. An apparatus as defined in claim 1 wherein said second sensing means has a zirconium oxide electrode.

11. An apparatus as defined in claim 1 wherein said second sensing means has a sample chamber and a reference chamber and wherein said second sensing means further comprises means for providing communication between the sample chamber and the reference chamber such that a change in the pressure within the sample chamber results in a corresponding change of pressure within the reference chamber so as to maintain the pressure within said chambers substantially equal at all times.

12. An apparatus for measuring the concentration of oxygen and carbon dioxide in expired gas from a patient, comprising:
   (a) a first inlet conduit for receiving expired gas from the respiratory system of a patient;
   (b) a second inlet conduit for receiving calibration gas;
   (c) an outlet conduit;
   (d) regulating means, positioned between said inlet conduits and said outlet conduit, for alternately regulating a continuous flow through said outlet conduit of one of said expired gas from the first inlet conduit or calibration gas from the second inlet conduit, said regulating means thereby serving to alternately allow passage of one gas at a time through said outlet conduit;
   (e) a cooler for cooling gas passing therethrough, said cooler being in gaseous communication with said outlet conduit so as to be positioned on the output side of said regulating means and said cooler serving to remove water from or add water vapor to the gas continuously flowing from said regulating means as needed to approximately equalize the water vapor pressure of each gas flowing through said cooler;
   (f) first sensing means in communication with the cooler for measuring the amount of carbon dioxide in the expired gas; and
   (g) second sensing means in communication with the cooler for measuring the amount of oxygen in the expired gas.

13. An apparatus as defined in claim 12 wherein the expired gas is received from the patient in a breath-by-breath mode.

14. A method for measuring the metabolic rate of a patient, the method comprising the steps of:
   (a) providing a first inlet conduit for receiving expired gas from the respiratory system of a patient, a second inlet conduit for receiving gas as inspired by the patient, and a third inlet conduit for receiving a calibration gas;
   (b) alternately introducing into a cooler a continuous flow from one of said inlet conduits such that said expired gas, said inspired gas, and said calibration gas are introduced one at a time into said cooler;

(c) cooling the gas within the cooler, the cooler serving to remove water from or add water vapor to the gas in said cooler as said gas continuously flows through said cooler;

(d) calibrating a carbon dioxide sensor using the calibration gas and inspired gas and sensing the amount of carbon dioxide in the expired gas and the inspired gas;

(e) calibrating an oxygen sensor using the calibration gas and sensing the amount of oxygen in the expired gas and the inspired gas; said oxygen sensor having a sample chamber and a reference chamber and said oxygen sensor further comprising means for providing communication between the sample chamber and the reference chamber such that a change in the pressure within the sample chamber results in a corresponding change of pressure within the reference chamber so as to maintain the pressure within said chambers substantially equal at all times; and (f) calculating the metabolic rate of the patient by comparing the amounts of carbon dioxide and oxygen in the expired gas with the amounts of carbon dioxide and oxygen in the inspired gas.

15. A method as defined in claim 14 wherein the cooler is configured with relatively narrow passageways so as to minimize the amount of gaseous volume within the cooler.

16. A method as defined in claim 14 wherein the cooler has a first horizontal passageway for carry in a a gaseous sample through the cooler, a second lower vertical passageway for continuously removing water which condenses within the cooler, and a third upper vertical passageway for removing the gaseous sample from the cooler.

17. A method as defined in claim 16 wherein the majority of the gaseous sample is removed through the third passageway of the cooler and wherein the remaining portion of the gaseous sample is removed through the second passageway of the cooler so as to assist in the removal of condensed water from the cooler.

18. A method as defined in claim 16 wherein about 80% of the gaseous sample is removed through the third passageway of the cooler and wherein the remaining portion of the gaseous sample is removed through the second passageway of the cooler so as to assist in the removal of condensed water from the cooler.

19. A method as defined in claim 16 further comprising the step of absorbing and continuously transporting condensed water from the cooler by disposing a wick within the second vertical passageway.

20. A method as defined in claim 14 wherein the cooler is a thermoelectric cooler.

21. A method as defined in claim 14 wherein the oxygen sensor has a zirconium oxide electrode.

22. An apparatus for measuring the metabolic rate of a patient, comprising:

(a) a first inlet conduit for receiving expired gas from the respiratory system of a patient;

(b) a second inlet conduit for receiving gas as inspired by the patient;

(c) a third inlet conduit for receiving a calibration gas;

(d) regulating means for alternately regulating a continuous flow of one of said expired gas from the first inlet conduit, inspired gas from the second inlet conduit, or calibration gas from the third inlet conduit;

(e) a cooler for cooling gas passing therethrough; said cooler being in gaseous communication with said regulating means and said cooler serving to remove water from or add water vapor to the gas continuously flowing from said regulating means as needed to approximately equalize the water vapor pressure of each gas flowing through said cooler;

(f) first sensing means in communication with the cooler for measuring the amount of carbon dioxide in a gaseous sample;

(g) second sensing means in communication with the cooler for measuring the amount of oxygen in a gaseous sample, said second sensing means having a sample chamber and a reference chamber and said second sensing means further comprising means for providing communication between the sample chamber and the reference chamber such that a change in the pressure within the sample chamber results in a corresponding change of pressure within the reference chamber so as to maintain the pressure within said chambers substantially equal at all times; and (h) means for comparing the amounts of carbon dioxide and oxygen in one gaseous sample with those in another gaseous sample.

* * * * *

UNITED STATES PATENT AND TRADEMARK OFFICE
CERTIFICATE OF CORRECTION

PATENT NO. : 4,572,208

DATED : February 25, 1986

INVENTOR(S) : Christopher A. Cutler et al.

It is certified that error appears in the above-identified patent and that said Letters Patent is hereby corrected as shown below:

Column 3, line 66, "washout time" should be --the washout time--
Column 6, line 10, "filter 61" should be --filter 64--
Column 7, line 44, "sensor 48,," should be --sensor 48,--
Column 10, line 5, "and a having" should be --having--
Column 12, line 68 - Column 13, line 1, "said expired gas, said expired gas" should be --said expired gas--
Column 13, line 33, "for carry in a a" should be --for carrying a--

Signed and Sealed this

Twenty-second Day of July 1986

[SEAL]

Attest:

DONALD J. QUIGG

Attesting Officer

Commissioner of Patents and Trademarks